United States Patent [19]

Wolfe et al.

[11] Patent Number: 4,962,238

[45] Date of Patent: Oct. 9, 1990

[54] REMOVAL OF GLYCOLS FROM A POLYALKYLENE GLYCOL DIALKYL ETHER SOLUTION

[75] Inventors: Ralph G. Wolfe, East Brunswick; Dennis P. Maloney, Morristown, both of N.J.; Robert E. Steele, Bunker Hill Village, Tex.; Constantine Tsonopoulos, Morristown, N.J.; Eugene R. Thomas, Houston, Tex.

[73] Assignee: Exxon Research and Engineering Company, Florham Park, N.J.

[21] Appl. No.: 417,112

[22] Filed: Oct. 4, 1989

[51] Int. Cl.$^5$ ............................................. C07L 41/38
[52] U.S. Cl. .................................................... 568/621
[58] Field of Search ......................................... 568/621

[56] References Cited

U.S. PATENT DOCUMENTS 4,322,312  3/1982  Boehnke ............................. 568/621
4,859,802  8/1989  Thomas ............................... 568/621

*Primary Examiner*—Howard T. Mars
*Attorney, Agent, or Firm*—Chris P. Konkol

[57] ABSTRACT

The removal of a glycol contaminant from a mixture of polyalkylene glycol dialkyl ethers is achieved using a dual solvent extraction process. The process is particularly applicable to removing glycols which accumulate in recirculating solutions of polyalkylene glycol dialkyl ethers used for the absorption of acid gases from feedstocks such as natural gas, synthetic natural gas, refinery gas, and ammonia synthesis gas.

26 Claims, 1 Drawing Sheet

REMOVAL OF GLYCOLS FROM A POLYALKYLENE GLYCOL DIALKYL ETHER SOLUTION

BACKGROUND OF THE INVENTION

The invention relates to a process for the purification of polyalkylene glycol dialkyl ether solutions contaminated with one or more glycols such as triethylene glycol.

In a number of chemical industries, mixtures of polyalkylene glycol dialkyl esters (hereinafter designated PG ethers) are conventionally used for absorbing acid gases, such as hydrogen sulfide and carbon dioxide, from gas mixtures such as natural gas, refinery gas, synthetic gas, ammonia synthesis gas, and the like. U.S. Pat. No. 3,737,392 to Ameen and Furbush discloses the treatment of a gas mixture by employing a recirculating solution of PG ethers to absorb acid gases from the gas mixture being treated. The absorbed acid gases are then removed from the PG ether solution by flashing.

A problem with the use of PG ether solutions is that they can become contaminated with chemical compounds which adversely effect their use. For example, glycol compounds from an upstream glycol dehydration process can contaminate PG ethers used in a downstream gas treating facility. Glycol dehydration is frequently used upstream of a natural gas treating facility to remove water from the natural gas by extracting the water therefrom with a glycol solvent. Glycol dehydration typically occurs prior to passing the natural gas through a pipeline to the gas treating facility, in order to prevent pipeline corrosion. Additionally, slugs of glycol may be periodically injected into the pipeline to further control corrosion. In the course of the dehydration operation, it has been found that some of the glycol is vaporized into the natural gas. Subsequently, in the gas treating facility, the glycol in the natural gas can be absorbed by a recirculating PG ether solution, used to treat the gas. Additionally, glycol may be carried into the PG ether solution by entrainment. In any case, the amount of glycol in the recirculating PG ether solution gradually builds up and may reach equilibrium concentrations as high as 35 percent.

The presence of a glycol contaminant in the PG ether solution has an adverse effect on its acid gas absorption capacity for which it is used in the gas treating facility. Additional recirculation is then required to achieve the same gas clean-up. This additional recirculation increases the operating expense of the gas clean-up, as well as decreasing the gas capacity of the gas treating facility. An alternate means to reduce the glycol contamination is to replace the PG ether solution with fresh solution. However, this is normally unacceptable due to the high cost of the PG ether solution.

It has been proposed to remove the glycol contaminant from the PG ether solution by distillation. Unfortunately, such a distillation would be undesirable due to the low pressures and high temperatures that would be required. Atmospheric conditions cannot be employed due to thermal stability limits on the PG ether solution. Additionally, such a distillation would entail a glycol purge that would involve substantial losses of the PG ether solution, especially desirable lower molecular weight components.

Several patents disclose the removal of various contaminants from a PG ether solution. For example, U.S. Pat. No. 4,334,102 to Decker et al discloses a method for removing liquid hydrocarbons. Decker et al utilizes an aqueous salt solution which is mixed with the contaminated PG ether solution in a tank. The aqueous phase is heated and separated into two phases in a vessel. The purified PG dimethyl ether solution is withdrawn from the vessel.

U.S. Pat. No. 3,831,348 to pap discloses a process to separate sulfur bearing compounds from PG ethers solutions. Pap utilizes low amounts of a water immiscible liquid hydrocarbon extracting solvent to achieve the desired separation.

The prior art processes for removing contaminants from a PG ether solution are not directly applicable when a glycol is the contaminant. Thus, the need exists for a process of removing glycol contaminants from a PG ether solution.

BRIEF DESCRIPTION OF THE INVENTION

It is a primary object of the present invention to provide a simple, efficient and economic process for the removal of glycols such as triethylene glycol from the solutions of polyalkylene qlycol dialkyl ether contaminated with such glycols. It is a further object of the present invention to provide a dual solvent extraction system for reducing the accumulation of glycols in a recirculating PG ether solution used in a gas treating facility for absorbing H$_2$S and other acid gases from natural gas or the like.

These and other objects are accomplished according to our invention, which comprises:

(1) contacting in an extraction zone a glycol contaminated polyalkylene glycol dialkyl ether feed with a solvent system comprising an organic solvent and an aqueous solvent;

(2) dividing the contents of the extraction zone into two phases, a first phase relatively rich in both said organic solvent and said polyalkylene glycol dialkyl ether solution and a second phase relatively rich in said aqueous solvent and said glycol;

(3) separating said first phase into two streams: a first stream relatively rich in organic solvent for recycle to said extraction zone and a second stream relatively rich in polyalkylene glycol dialkyl ethers and, with respect to the feed, depleted in glycols; and (4) separating said second phase into two streams: a relatively glycol rich stream which is purged from further use in said extraction zone and a relatively glycol depleted aqueous stream for recycle to the extraction zone.

In preferred forms of the invention, the organic solvent is selected such that the flow ratio of organic solvent to the PG ether solution introduced into the extraction zone is less than or equal to about 3 to 1.

BRIEF DESCRIPTION OF THE DRAWING

The process of the present invention will be more clearly understood upon reference to the detailed discussion below and to FIG. 1 (the sole drawing) which is a flow diagram illustrating one preferred embodiment for practicing the present invention. In particular.

DETAILED DESCRIPTION OF THE INVENTION

Figure 1:
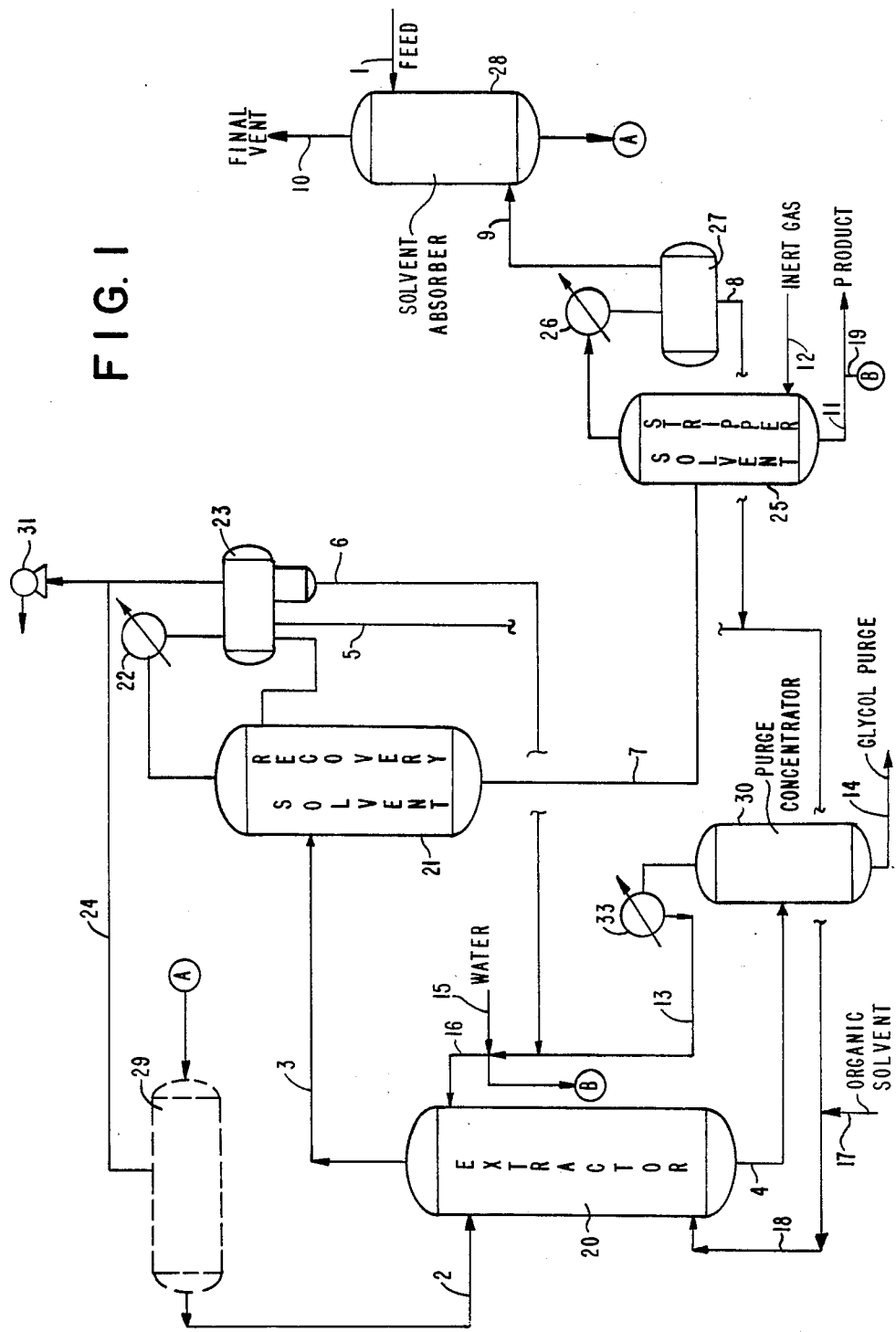
FIG. 1 illustrates a dual solvent extraction process which removes glycol contaminants from a polyalklylene glycol dialkyl ether solution.

The process of the present invention accomplishes the removal of glycol contaminants from a polyalkylene glycol dialkyl ether solution (hereinafter designated a PG ether solution). The process employs a dual solvent system comprising an aqueous solvent and an organic solvent. The organic solvent is selected such that it is essentially immiscible in the aqueous solvent, but has a high solubility for PG ethers. The function of the organic solvent is to extract the PG ethers from the contaminated PG ether feed. The aqueous solvent is selected such that it is essentially immiscible in the organic solvent, but has a high solubility for the glycol contaminants. The function of the aqueous solvent is to extract the glycol contaminants from the PG ether feed. This dual solvent approach achieves separation of glycols from the PG ethers, while minimizing the loss of any PG ethers in the aqueous solvent.

By the term organic solvent is meant a carbon containing compound which is liquid at ambient conditions having properties such as polarity resulting in a selectively high solubility for PG ethers compared to glycols. Polarity may be estimated through published solubility parameters. However, the selectivity of a solvent typically needs to be determined through routine solubility experiments. In addition, the organic solvent must have an adequate density difference from the aqueous solvent for easy phase disengagement, and it must be readily separable from the polyalkylene glycol dialkyl ether by distillation. Other considerations in selecting a solvent are thermal stability and low toxicity. Preferred solvents are those having solubility parameters between 6.8 and 9.7 and having normal boiling points primarily between 100° and 400° F. Illustrative of preferred solvents are paraffins such as isooctane, cyclic hydrocarbons such as cyclohexane, aromatics such as toluene, chlorinated hydrocarbons such as methylene chloride, and the like or mixtures thereof. Refinery reformate is also suitable.

Preferably the organic solvent should be highly effective and efficient in selectively separating the PG ethers from the glycols. Otherwise, impracticable amounts of solvent may be necessary. In the preferred embodiment, the ratio of organic solvent to PG ether feed introduced into the extraction zone is less than 10:1, preferably less than 4:1. The ratio of the organic solvent to the aqueous solvent is suitably 100:1 to 1:1, preferably 20:1 to 3:1.

By the term "aqueous solvent" in the following description is meant any solvent comprising water. The strong polarity and other properties of water confer a selectively high solubility for glycols as compared to PG ethers.

By the term "alkyl" is meant branched or unbranched groups of 1 to 6 carbon atoms, for example ethyl, propyl, butyl, pentyl, or hexyl.

By the term "alkylene" is meant hydrocarbon groups of 2 to 4 atoms, for example, ethylene, propylene, or butylene.

The present invention is applicable to polyalkylene glycol dialkyl ether solutions in general, but is particularly applicable to a PEG ether composition (a polyethylene qlycol dimethyl ether mixture), for example of the kind disclosed in U.S. Pat. No. 3,737,392 to Ameen et al. This composition is commercially available from Norton Chemical Process Products (Akron, Ohio) and is sold under the registered trademark SELEXOL. It is essentially a mixture of dimethyl ethers of polyethylene glycols of the formula $CH_3O(C_2H_4O)_xCH_3$ wherein x is between 3 and 9. The homolog distribution is approximately as follows:

| x | wt. percent |
|---|---|
| 3 | 4–9 |
| 4 | 22–24 |
| 5 | 24–28 |
| 6 | 20–22 |
| 7 | 13–15 |
| 8 | 6–8 |
| 9 | 2–4 |

Minor amounts of lower and higher homologues may also be present. The physical properties of SELEXOL solvent are disclosed in *Gas Purification,* Kohl, Arthur and Riesenfeld, Fred, Gulf publishing Co, Houston (1985) at page 85.

Referring to FIG. 1, a flow diagram illustrating the present process for separating glycols from a PG ether solution is shown. Conventional control valves, pumps, and the like have not been shown in FIG. 1 for the sake of clarity. A contaminated PG ether feed stream 2, enters the extractor 20 where removal of glycols from the PG ether solution is accomplished. A dual solvent system comprising an organic solvent stream 18 and an aqueous solvent stream 16 enters the extractor 20. Make-up organic solvent is introduced via stream 17. As shown in FIG. 1, the organic solvent is introduced into the bottom of the extractor 20, while the aqueous solvent is introduced into the top. A light phase product equilibrates to the top of the extractor, which light phase is made up principally of the organic solvent and the PG ethers. A heavy phase product which equilibrates to the bottom of the extractor is made up principally of the the aqueous solvent and glycols in the feed. Generally, the contacting, mixing, and separation may be performed in conventional solvent extraction equipment. For example, continuous countercurrent multistaged or column solvent extraction may be used. The operating parameters of the extractor may be optimized for integration into the present process. Operating pressures are set to prevent excessive vaporization in the extractor. Temperatures between 32° F. and 400° F. are suitable.

The light phase PG ether/organic solvent rich stream 3 exits the extractor 20 and enters an organic solvent recovery means 21 which operates to recover the organic solvent for recycle back to the extractor 20. The organic solvent recovery means 21 comprises a fractionation or distillation zone that operates under vacuum, by means of a vacuum vent created by vacuum pump 31. Recovery of the organic solvent is maximized while not exceeding the temperature limitation of the PG ethers. An upper temperature limit of 400° F. and preferably 360° F. is maintained in the organic solvent recovery means 21. A suitable pressure range is about 2 to 15 psia. The organic solvent is recycled as stream 5 back to the extractor 20 via the condensor 22 and collector 23. Depending on the site water balance, the aqueous phase which collects at the bottom of the collector 23, may be recycled to the extractor 20 as water recycle stream 6.

The PG ether rich bottoms stream 7 from the organic solvent recovery means 21 may still contain a significant amount of organic solvent. Ideally, the organic content for purified PG ether solution would be nil, since any of the organic solvent present in the PG solvent when returned to the gas treating facility may eventually reach the sulfur plant, where it may adversely affect operations. Therefore, the bottoms stream 7 from the organic solvent recovery means 21 is preferably stripped with an inert gas stream 12 in an organic solvent stripper 25 to reduce the organic solvent content of the PG ether to less than 1 ppm and yield a purified PG ether product stream 11. Water in stream 19 may be introduced to obtain the desired concentration. The stripping gas which enters the stripper 25 is suitably nitrogen, carbon dioxide, or any available gas, for example natural gas and the like. The organic solvent stripper 25 comprises conventional equipment, for example, a tower or column containing trays or packing. The temperature in the stripper is ambient or appropriately elevated to promote vaporization of the organic solvent. A suitable pressure range is 1 to 100 psig and a suitable temperature range is 32° to 400° F.

The vent gas stream 9 from the organic solvent stripper 25 passes through a condensor 26 and collector 27, which collects organic solvent and sends it via stream 8 for recycle to the extractor 20. The vent gas stream 9 continues to an organic solvent absorber 28 to recover any remaining organic solvent before final venting in stream 10. Advantageously, the organic solvent is recovered by scrubbing the gas with the contaminated PG ether feed in stream 1, arriving from the gas treating facility, prior to its introduction into the extractor 20. The temperature of the feed stream 1 to the absorber can be controlled to the desired value by blending the contaminated PG ether solution streams from various locations in the gas treating facility, as more fully described below.

The absorber bottoms stream 2 from the absorber 28, which stream comprises the contaminated PG ether solution, is saturated with stripping gas. To avoid possible problems upon introduction into the extractor 20, a vacuum degasser 29 may be employed. The vacuum degasser 29 vents into an overhead gas stream 24 and vacuum pump 31, in common use with the organic solvent recovery means 21.

Returning to the extractor 20, the heavy phase glycol rich phase in the extractor 20 is withdrawn as stream 4 and subsequently introduced into a glycol purge concentrator 30 to recover aqueous solvent for recycle back to the extractor. The glycol purge concentrator operates suitably at a pressure above atmospheric, the upper limit being set by the reboiler heat source in order to avoid vacuum equipment. The bottoms stream 14 comprises the glycol purge. The overhead glycol depleted aqueous solvent stream 13 is recycled back to the extractor via condensor 33. Make-up aqueous solvent to replace the amount purged may be added via line 15. If sufficient water is available on site to satisfy the extractor requirements without water recovery from the glycol purge concentrator, then the heavy phase extractor product, water plus glycol, might be purged directly and the purge concentrator 30 deleted. Similarly, the above mentioned absorber 28 might be deleted depending on the amount of purge permitted by environmental concerns or economic constraints.

As mentioned above, the purified PG ether is typically returned to a gas treating facility where it is used to remove acid gases such as $H_2S$ from a gaseous mixture such as natural gas. Said gaseous mixture is first contacted in at least one contacting or absorption zone under superatmospheric pressure with the PG ether solution to effect absorption of the acid gases, thereby purifying the gaseous mixture. The PG ether solution containing the dissolved acid gas from the absorption zone is typically passed to a flashing zone maintained at a pressure substantially lower than that in the first absorption zone to effect liberation of components of the treated gaseous mixture. The flash may be enhanced by using an inert stripping gas such as nitrogen. The PG ether solution from the flashing zone is sent to an acid gas regeneration zone, for example a heated regeneration section comprising a multi-stage distillation tower. The regeneration zone purifies the PG ether solution of acid gases so that it may be recirculated back to the absorption zone for further use in treating a gaseous mixture. The PG ether solution containing stream returning to the absorption zone from the regeneration zone, typically from the area of the distillation tower bottoms, is called the acid gas regenerator bottoms stream. This stream is the preferred source for removing the glycol contaminated PG ether for treatment according to the present invention, since the acid gas regenerator bottoms stream does not contain $H_2S$. Therefore, the problems associated with handling a stream containing $H_2S$, particularly toxicity, are avoided. Further, the acid gas regenerator bottoms stream does not contain other dissolved gases, for example methane, carbon dioxide or the like and there may therefore be no need to operate the extractor under pressure to prevent gas evolution or to provide degassing and gas handling facilities either before the extractor or before the organic solvent recovery means. An additional advantage of taking the acid gas regenerator bottoms stream is that it is available over a wide range of temperature and any desired feed temperature can be obtained by blending, thereby eliminating the need for additional heat exchange equipment. With respect to a gas treating facility, see generally *Gas Purification*, Kohl, Arthur and Riesenfeld, Fred, Gulf publishing Co, Houston (1985) at page 85. Other energy conservation techniques will be apparent to those skilled in the art.

EXAMPLE 1

This example illustrates the evaluation of an organic solvent for extraction of a glycol, namely triethylene glycol, using isooctane as the solvent. Isooctane has a solubility parameter of about 6.9. Into a 100 ml centrifuge tube, 25 parts by volume of a contaminated SELEXOL PG ether solution is added to 75 parts isooctane. The contaminated SELEXOL PG ether solution was composed of 91wt. % virgin SELEXOL PG ether solution, 6.5% triethylene glycol (TEG) and 2.5% water. The contaminated SELEXOL PG ether solution therefore had 14 parts of the SELEXOL PG ether solution per part of TEG. The tube was shaken for 2 minutes and centrifuged for two minutes to disengage the phases. The concentration of the lower aqueous phase was measured and found to have the following composition: 1.8 wt. % water, 6.9% isooctane, 7.9% TEG, and 83.4% SELEXOL PG ether solution. The lower phase therefore had 10.6 parts SELEXOL PG ether solution per part TEG. The ratio of isooctane used to the contaminated SELEXOL PG ether solution was 3 by volume.

EXAMPLE 2

This example illustrates that staging and additional solvent amounts can further concentrate a glycol contaminant in an aqueous solvent. The upper phase of the centrifuge of Example 1 above was removed. To the lower phase was added enough isooctane (77.5 ml) to bring the total volume to 100 ml. The centrifuge tube was shaken and centrifuged. The upper phase was removed. This was repeated eleven more times. The final lower phase compostion was measured and the following found: 22 wt. % water, less than 2% isooctane, 58% TEG and 20% SELEXOL PG ether solution. The lower phase therefore had 0.35 parts SELEXOL PG ether solution per part of TEG. However, the ratio of total isooctane added to the contaminated SELEXOL PG ether solution was about 47 by volume, which may be higher than desirable for large scale industrial use.

EXAMPLE 3

This example illustrates the advantage of the dual solvent approach according to the present invention. Toluene is more polar than isooctane and has a solubility parameter of about 8.9. To a 250 ml stirred extractor was added 45.2 g of a contaminated SELEXOL PG ether solution, 81.8 g toluene, and 1.6 g of water. The composition was mixed at 112° F and the phases disengaged. The lower aqueous phase composition was measured and found to comprise the following: 35.6 wt. water, 1.7% toluene, 46.5% TEG, and 16.2% SELEXOL PG ether solution. The lower phase therefore had 0.35 parts SELEXOL PG ether solution per part of TEG. The ratio of added toluene to the contaminated SELEXOL ethers was 1.8 by weight. The lower phase was estimated to be about 3.9 g, indicating that 47% of the initial TEG was removed from the bulk of the contaminated SELEXOL PG ether solution in this single extraction stage.

EXAMPLE 4

This example illustrates that any PG ether purged by solvent extraction tends to be the less valuable higher molecular weight components. To 45.2 g of a contaminated SELEXOL PG ether solution, were added 81.8 g of toluene and 1.6 g of water. The components were mixed at 72° F. and the phases disengaged. The compositions of the upper and lower phases were measured and found to have the following compositions.

| Component | Composition, wt % | |
| --- | --- | --- |
| | Upper Phase | Upper Phase |
| Triethylene glycol-dimethyl ether | 3.30 | 2.62 |
| Tetraethylene glycol-dimethyl ether | 9.07 | 8.48 |
| Pentaethylene glycol-dimethyl ether | 11.41 | 12.20 |
| Hexaethylene glycol-dimethyl ether | 9.20 | 11.21 |
| Heptaethylene glycol-dimethyl ether | 5.54 | 7.75 |
| Octaethylene glycol-dimethyl ether | 2.64 | 4.23 |
| Nonaethylene glycol-dimethyl ether | 1.01 | 1.91 |
| Decaethylene glycol-dimethyl ether | 0.32 | 0.73 |
| Undecaethylene glycol-dimetyhyl ether | 0.08 | 0.23 |

EXAMPLE 5

This example illustrates that chlorinated hydrocarbons can also be used in a dual solvent approach. To a mixture of 60 parts SELEXOL PG ether solution and 13 parts TEG was added 13 parts methylene chloride and 14 parts water. Methylene chloride has a solubility parameter near 9.7. Two phases were formed, the bottom phase representing 35% of the total volume. While this bottom phase was not precisely analyzed for composition, because of the relative polarity of the compounds and the phase volumes, it was estimated to be primarily water and TEG.

EXAMPLE 6

This process design is based on literature correlations and typical design criteria. The stream numbers in this example correspond to the stream numbers in FIG. 1. In this example, parts and percentages are by weight unless otherwise specified. SELEXOL is a registered trademark for an indistrual solvent product sold by Norton Chemical Process Products (Akron, Ohio). This product (hereafter "SELEXOL PG ether solution") consists of a polyethylene glycol dimethyl ether solution.

The design in this example corresponds to a toluene to contaminated SELEXOL PG ether solution treat rate ratio of 3 lb/lb and a water to contaminated SELEXOL PG ether solution treat rate ratio of 0.4 lb/lb. The contaminated SELEXOL PG ether solution from the gas treating facility has a flow rate of 100 lbs/hr with a TEG content of 15%. The contaminated SELEXOL ether feed 1 comprising 82 parts SELEXOl ethers, 15 parts TEG, and 3 parts water are introduced into a toluene absorber 28. Here the SELEXOL ether solution serves to cleanse the process vent gas of toluene, as will be more fully explained below. The bottoms stream 2 from the absorber 28 is introduced into a multi-stage extractor 20 as feed stream 2. The extractor is operated at a temperature near 100° F. and a pressure near 22 psia. The toluene rich extractor product in stream 3 comprises 77.59 parts SELEXOL ethers, 0.20 parts TEG, 0.41 parts water and 21.80 parts toluene representing a total rate of 390 lb/hr. The extractor water rich product stream 4 comprises 3.93 parts SELEXOL ethers, 25.21 parts TEG, 70.65 parts water, and 0.21 parts toluene representing a rate of 57 lb/hr.

The toluene recovery tower has associated therewith a reboiler and condensor. Various pumps are also associated with the toluene recovery tower 21, including a reflux toluene recycle pump to handle reflux stream 5. A distillate drum water pump handles stream 6 and a the bottoms product pump handles stream 7. Also, a vacuum pump is used to provide a vacuum in the toluene recovery tower 21. The toluene recycle stream 5 comprises essentially 99.6 part toluene and 0.4 parts water, representing a flow rate of 299 lb/hr. This stream 5 is joined by make-up toluene stream 17 comprising 100 percent toluene. The streams 17 and 5 together comprise a toluene feed stream 18 to the extractor 20 comprising 1.68 parts SELEXOL ethers, 0.07 parts TEG, 0.041 parts water, and 97.84 parts toluene. This combined stream 18 has a flow rate of 305 lb/hr.

The water recycle stream 6 from the toluene recovery column 21, comprising 100% water at a flow rate of 0.4 lb/hr.

The toluene recovery bottoms stream 7 is introduced as feed to the toluene stripper 25. The toluene stripper is a column having associated therewith a condensor, a pump to transport the toluene recycle distillate, and a pump to transport the purified SELEXOL ether solution. A nitrogen stripping gas is supplied to the toluene stripper as gas stream 12 at a rate of 272 lb/hr. The main product from the toluene stripper 25 is the purified SELEXOl ether product comprising 92.27 parts SELEXOL ethers and 0.73 parts TEG at a flow rate of 80 lb/hr. The toluene stripper 25 also produces a second toluene recycle stream 8 comprising 92.44 parts SELEXOL ethers, 3.59 parts TEG and 3.97 parts toluene. The pressure is 20.0 psia and the temperature is 110° F. The vent stream 9 from the stripper 25 comprises 0.04 parts SELEXOL ethers, 1.85 parts toluene and 98.11 parts nitrogen. The vent stream 9 is introduced into toluene absorber 28, described above, where it is contacted with the contaminated SELEXOL ether solution to remove any remaining toluene from the nitrogen gas in the final vent gas stream 10. The final vent gas stream 10 from the toluene absorber 27 comprises 0.88 parts water, 0.21 parts toluene, and 98.90 parts nitrogen.

The SELEXOL ether solution bottoms stream 2 from the toluene absorber comprises 92.27 parts SELEXOL and 0.73 parts TEG representing a flow rate of 102 lb/hr. It is sent to the extractor 20 as feed stream 2, optionally via a degassing drum or tower.

The bottoms stream 4 from the extractor 20, which is water rich, is introduced into a TEG purge concentrator 30 with associated condensor and reboiler. The bottoms from the concentrator is the TEG purge stream 14 and is 12.94 parts SELEXOL ethers, 85.53 parts TEG and 1.53 parts water. The top product stream 13 of the concentrator 30 is the second water recycle stream to the extractor 20 comprising 0.19 parts SELEXOL ethers, 0.02 parts TEG, 99.49 parts water, and 0.30 parts toluene for a total flow rate of 40 lb/hr.

Pumps are used to transport the TEG purge bottoms 14 and the recycle water distillate stream 13.

The recycle water distillate stream 13 from the TEG purge concentrator is joined by make-up water stream 15. The combined streams 13 and 15 result in a total water stream 16 to the extractor 20 comprising 0.13 parts SELEXOL ethers, 0.03 parts TEG, 99.5 parts water and 0.29 parts toluene. Stream 16 is at a temperature of 110° F. and a pressure of 100 psia. The material balance and operating conditions for the above described design are given in Table I below.

TABLE 1

TEG REMOVAL VIA TOLUENE EXTRACTION MATERIAL BALANCE

| STREAM NO. | 1 | 2 | 3 | 4 | 5 | 6 |
|---|---|---|---|---|---|---|
| DESCRIPTION | CONTAMINATED SELEXOL FEED | ABSORBER BOTTOMS/ EXTRACTOR FEED | EXTRACTOR TOLUENE RICH PRODUCT | EXTRACTOR WATER RICH PRODUCT | RECYCLE TOLUENE I | RECYCLE WATER I |
| COMPOSITION, WT % | | | | | | |
| SELEXOL | 82.00 | 80.31 | 77.59 | 3.93 | TR | TR |
| TEG | 15.00 | 14.68 | 0.20 | 25.21 | TR | TR |
| WATER | 3.00 | 0.57 | 0.41 | 70.65 | 0.4 | 100.0 |
| TOLUENE | — | 4.44 | 21.80 | 0.21 | 99.6 | TR |
| $N_2$ | | | | | | |
| RATE, #/HR | 100 | 102 | 390 | 57 | 299 | 0.4 |
| TEMPERATURE, °F. | 110 | 100 | 105 | 110 | 110 | 110 |
| PRESSURE, PSIA | 200 | 22 | 200 | 200 | 8.0 | 8.0 |

| STREAM NO. | 7 | 8 | 9 | 10 | 11 | 12 | 13 |
|---|---|---|---|---|---|---|---|
| DESCRIPTION | TOLUENE RECOVERY BTMS/STRIP FEED | RECYCLE TOLUENE II | TOLUENE STRIPPER VENT | $N_2$ FINAL VENT | CLEAN SELEXOL PRODUCT[2] | STRIPPING GAS | RECYCLE WATER II[2] |
| PROCESS COMPOSITION, WT % | | | | | | | |
| SELEXOL | 93.26 | 92.44 | 0.04 | TR | 92.27 | — | 0.19 |
| TEG | 0.87 | 3.59 | TR | TR | 0.73 | — | 0.02 |
| WATER | — | — | — | 0.88 | — | — | 99.49 |
| TOLUENE | 5.87 | 3.97 | 1.85 | 0.21 | — | — | 0.30 |
| $N_2$ | | | 98.11 | 98.90 | — | 100.0 | — |
| RATE #/HR | 91 | 5.5 | 277 | 274 | 80.3 | 272 | 40 |
| TEMPERATURE, °F. | 360 | 110 | 110 | 98 | 100 | 100 | 110 |
| PRESSURE, PSIA | 11.0 | 20.0 | 20.0 | 18.0 | 22 | 100 | 20 |

| STREAM NO. | 14 | 15 | 16 | 17 | 18 | 19 |
|---|---|---|---|---|---|---|
| DESCRIPTION | TEG PURGE | MAKE-UP WATER | WATER TO EXTRACTOR | MAKE-UP TOLUENE | TOLUENE TO EXTRACTOR | WATER TO GAS |
| PROCESS COMPOSITION, WT % | | | | | | |
| SELEXOL | 12.94 | — | 0.13 | — | 1.68 | 0.13 |
| TEG | 85.53 | — | 0.03 | — | 0.07 | 0.03 |
| WATER | 1.53 | 100.0 | 99.55 | — | 0.41 | 99.55 |
| TOLUENE | — | — | 0.29 | 100.0 | 97.84 | 0.29 |
| $N_2$ | — | — | — | — | — | — |
| RATE #/HR | 17 | 3 | 40 | 0.6 | 305 | 3 |
| TEMPERATURE, °F. | 375 | 110 | 110 | 110 | 110 | 110 |
| PRESSURE, PSIA | 21 | 100 | 100 | 100 | 100 | 100 |

Various modifications will be apparent to one skilled in the art, and it is not intended that this invention be limited to details presented by way of illustration, except as required by express limitations in the appended claims.

What is claimed is:

1. A process for the purification of a solution comprising a polyalkylene glycol dialkyl ether or mixtures thereof which comprises:
   (1) contacting in an extraction zone a glycol contaminated polyalkylene glycol dialkyl ether solution with a solvent system comprising an organic solvent and an aqueous solvent;

(2) dividing the contents of the extraction zone into two phases, a first phase relatively rich in both said organic solvent and said polyalkylene glycol dialkyl ether solution and a second phase relatively rich in said aqueous solvent and said glycol; and (3) separating said first phase into two streams: a first stream relatively rich in organic solvent for recycle to said extraction zone and a second stream relatively rich in polyalkylene glycol dialkyl ether and, with respect to the feed, depleted in glycols.

2. The process of claim 1, further comprising separating said second phase into two streams: a relatively glycol rich stream which is purged from further use in said extraction zone and a relatively glycol depleted aqueous stream for recycle to the extraction zone.

3. The method of claim 1, wherein the polyalkylene glycol dialkyl ether comprises an alkyl of 1 to 5 carbons and an alkylene of 2 to 6 carbons.

4. The method of claim 3, wherein the alkyl is methyl.

5. The process of claim 3, wherein the alkylene is ethylene.

6. The process of claim 1, wherein the polyalkylene glycol dialkyl ether solution is a mixture of ethers of the formula $CH_3(OCH_2CH_2)_xOCH_3$ wherein x is between 3 and 8 for at least 95 mol percent of the mixture.

7. The process of claim 1, wherein the organic solvent in the dual solvent system has a higher solubility selectivity for polyalkylene glycol dialkyl ethers than for glycols.

8. The process of claim 1, wherein the organic solvent is a compound or mixture of compounds having a solubility parameter ranging from about 6.8 to 9.7.

9. The process of claim 8, wherein the organic solvent has a boiling point between about 100° and 400° F.

10. The process of claim 1, wherein the organic solvent is toluene.

11. The process of claim 1, wherein the glycol is selected from the group consisting of triethylene glycol, diethylene glycol, and tetraethylene glycol and mixtures thereof.

12. The process of claim 1, wherein said organic solvent rich stream is separated from said polyalkylene glycol dialkyl ether rich stream in a distillation zone.

13. The process of claim 12, wherein the polyalkylene glycol dialkyl ether rich stream is further recovered in a stripping zone.

14. The process of claim 13, wherein the polyalkylene glycol dialkyl rich stream is stripped with an inert gas selected from the group consisting of nitrogen, natural gas, carbon dioxide, fuel gas, or air.

15. The process of claim 14, wherein the vent gas from the stripping zone is further contacted with contaminated polyalkylene glycol dialkyl ether solution prior to said solution being introduced into the extracting zone.

16. The process of claim 13, wherein the purified final polyalkylene glycol alkyl ether product for returning to a gas treating facility is the bottoms product of the stripping zone.

17. The process of claim 1, wherein the contaminated polyalkylene glycol dialkyl ether solution is first degassed prior to being introduced into the extracting zone.

18. The process of claim 1, wherein the glycol content in the contaminated polyalkylene glycol dialkyl ether solution feed is about 3 to about 35 weight percent.

19. The process of claim 1, wherein the glycol content in the purified product is less than about 5 weight percent.

20. The process of claim 1, wherein the ratio of organic solvent to aqueous solvent is about 20:1 to about 3:1.

21. The process of claim 1, wherein the polyalkylene glycol dialkyl ether solution has a greater solubility in the organic solvent than the aqueous solvent.

22. The process of claim 1, wherein the glycols to be removed have a higher solubility in the aqueous solvent than the organic solvent.

23. The process of claim 1, wherein the polyalkylene glycol dialkyl ether solution feed stream is obtained from the acid gas regenerator bottoms stream of a gas treating facility for removing acid gases from the gas being treated.

24. A process for the purification of a solution comprising a polyethylene glycol dimethyl ether or mixtures thereof which comprises:

(1) contacting in an extraction zone a glycol contaminated solution comprising polyethylene glycol dimethyl ethers with a solvent system comprising an aqueous solvent and an organic solvent selected from the group consisting of compounds having a solubility parameter between about 8 and 9.4 and a boiling point between about 100° and 400° F.;

(2) dividing the contents of the extraction zone into two phases, a first phase relatively rich in both said organic solvent and said polyethylene glycol dimethyl ether solution and a second phase relatively rich in said aqueous solvent and said glycol; and (3) separating said first phase into two streams: a first stream relatively rich in organic solvent for recycle to said extraction zone and a second stream relatively rich in polyethylene glycol dimethyl ethers.

25. The process of claim 24, further comprising separating said second phase into two streams: a relatively glycol rich stream which is purged from further use in said extraction zone and a relatively glycol depleted aqueous stream for recycle to the extraction zone; and whereby the flow ratio to the extraction zone of the organic solvent to the feed is less than or equal to about 3 to 1.

26. A process for the purification of solution comprising a polyalkylene glycol dialkyl ether or mixtures thereof which comprises:

(1) contacting in an extraction zone a glycol contaminated polyalkylene glycol dialkyl ether feed solution with a solvent system comprising an organic solvent and an aqueous solvent;

(2) dividing the contents of the extraction zone into two phases, a first phase relatively rich in both said organic solvent and said polyalkylene glycol dialkyl ether solution and a second phase relatively rich in said aqueous solvent and said glycol;

(3) separating in a distillation zone said first phase into two streams: a first stream relatively rich in organic solvent for recycle to said extraction zone and a second stream relatively rich in polyalkylene glycol dialkyl ether;

(4) separating said second phase into two streams: a relatively glycol rich stream which is purged from further use in said extraction zone and a relatively glycol depleted aqueous stream form recycle to the extraction zone; and (5) purifying in a stripping zone the polyalkylene glycol dialkyl ether by contacting the same with a stripping gas to absorb therefrom remaining organic solvent.

* * * * *